United States Patent
Johnson et al.

(10) Patent No.: US 6,787,603 B2
(45) Date of Patent: Sep. 7, 2004

(54) METHOD OF MAKING EMULSION CONTAINING QUATERNARY AMMONIUM FUNCTIONAL SILANES AND SILOXANES

(75) Inventors: Bethany K. Johnson, Midland, MI (US); Zuchen Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/306,012

(22) Filed: Nov. 27, 2002

(65) Prior Publication Data

US 2004/0102570 A1 May 27, 2004

(51) Int. Cl.⁷ .................. C08L 83/00; C08G 77/26
(52) U.S. Cl. ................ 524/838; 524/837; 528/25; 528/27; 528/38
(58) Field of Search ................ 524/837, 838; 528/25, 27, 38

(56) References Cited

U.S. PATENT DOCUMENTS

| | | | |
|---|---|---|---|
| 5,389,364 A | 2/1995 | Cifuentes et al. | 424/70.122 |
| 5,409,695 A | 4/1995 | Abrutyn et al. | 424/70.12 |
| 5,419,627 A | 5/1995 | Oldinski | 312/114 |
| 5,504,149 A | 4/1996 | Kosal | 524/837 |
| 5,948,855 A | 9/1999 | Lin et al. | 524/837 |
| 6,071,975 A | 6/2000 | Halloran | 516/58 |
| 6,475,974 B1 | 11/2002 | Leboucher et al. | 510/417 |
| 6,482,969 B1 * | 11/2002 | Helmrick et al. | 556/420 |

FOREIGN PATENT DOCUMENTS

JP   2002308991 A  * 10/2002  ......... C08G/77/388

OTHER PUBLICATIONS

Application No.: 10/001,760, filed Oct. 24, 2001, our Docket No.: DC4900, entitled "Silicon Based Quaternary Ammonium Functional Compositions and Methods for Making Them", Liza Ruth Helmrick and John Joseph Kennan, in the name of Dow Corning Corporation, now US Patent # 6,482,969 Hemrick et al.

Application No.: 10/001,753, filed 10/24/2001, our Docket No.: DC4937, entitled "Silicon Based Quaternary Ammonium Functional Compositions and Their Applications", Bethany K. Johnson, John Joesph Kennan, and Feifei Lin, in the name of Dow Corning Corporation, non US Patent # 6,07,717 Johnon et al.

* cited by examiner

Primary Examiner—Margaret G. Moore
Assistant Examiner—Marc S. Zimmer
(74) Attorney, Agent, or Firm—Jim L. De Cesare

(57) ABSTRACT

Oil-in-water (O/W) and water-in-oil (W/O) emulsions and microemulsions containing silanes or siloxanes having quaternary ammonium groups are made by reacting organic quaternary ammonium compounds having epoxide groups or halohydrin groups, with silanes or siloxanes having amino groups. The reaction is carried out in an aqueous polar phase containing a surfactant. The emulsions and microemulsions are especially useful for treating hair, skin, or the underarm.

8 Claims, No Drawings

METHOD OF MAKING EMULSION CONTAINING QUATERNARY AMMONIUM FUNCTIONAL SILANES AND SILOXANES

FIELD OF THE INVENTION

This invention is directed to a method of making oil-in-water (O/W) emulsions and microemulsions and water-in-oil (W/O) emulsions and microemulsions containing silanes or siloxanes having quaternary ammonium groups as an oil phase. In particular, the silanes or siloxanes are obtained by reacting organic quaternary ammonium compounds having epoxide or halohydrin groups, with silanes or siloxanes having amino groups; and the reaction is carried out in the presence of a surfactant in an aqueous polar phase.

BACKGROUND OF THE INVENTION

Copending application U.S. Ser. No. 10/001,760, filed Oct. 24, 2001, entitled Silicon Based Quaternary Ammonium Functional Compositions and Methods for Making Them (the 760 application); and copending application U.S. Ser. No. 10/001,753, filed Oct. 24, 2001, entitled Silicon Based Quaternary Ammonium Functional Compositions and Their Applications (the '753 application), are both assigned to the same assignee as the present application, and incorporated herein by reference.

As noted in the '753 and '760 applications, quaternary ammonium functional silanes and quaternary ammonium functional siloxanes have a variety of commercial application in the textile industry and in the personal care arena They can also be used as anti-microbial agents; in modifying fillers, fibers, and surfaces; as thickening agents; and as a conditioning agent.

In many of these applications and uses, it is often necessary to deliver the quaternary ammonium functional silanes and the quaternary ammonium functional siloxanes as an emulsion or microemulsion. When an emulsion is required, conventional wisdom dictates that the quaternary ammonium functional silane or quaternary ammonium functional siloxane be combined with a surface active agent and water, and mixed until the emulsion is formed.

It is often inconvenient for end users of quaternary ammonium functional silanes and siloxanes to prepare emulsions and microemulsions, and so it would be beneficial to provide a new and simpler process for preparing the emulsions.

While the '753 application describes a method of making emulsions containing quaternary ammonium functional silanes and quaternary ammonium functional siloxanes, the process involves application of conventional wisdom, i.e., the quaternary ammonium functional silane or siloxane is combined with a surface active agent and water, and mixed until an emulsion is formed.

The process according to the present application however, differs significantly from the process used in the '753 application, in that quaternary ammonium functional silanes or siloxanes are actually synthesized in an emulsion, using monomers as starting materials which are reacted together to form the quaternary ammonium functional silane or siloxane, rather than using quaternary ammonium functional silanes or siloxanes.

SUMMARY OF THE INVENTION

This invention relates to methods of making certain oil-in-water (O/W) or water-in-oil (W/O) emulsions and microemulsions containing organosilicon compositions as the oil phase. In particular, these emulsions and microemulsions contain silanes or siloxanes having quaternary ammonium groups in their molecule as the oil phase, the silanes or siloxanes having quaternary ammonium groups having been obtained by reacting (i) an organic quaternary ammonium compound having epoxide groups or halohydrin groups in its molecule, with (ii) a silane or siloxane having amino groups in its molecule, in the presence of (iii) a surfactant, components (i)–(iii) being dispersed in (iv) an aqueous polar phase.

Representative of suitable quaternary ammonium compounds having epoxide groups and halohydrin groups are glycidyl trimethylammonium chloride, and (3-chloro-2-hydroxypropyl)trimethylammonium chloride, respectively. The aqueous polar phase may consist of water, it may comprise a mixture of water and a volatile low molecular weight polysiloxane, or it may be a mixture of water and a polar organic compound such as 1,2-hexanediol. These emulsions and microemulsions are useful as treating agents for the hair, skin, and the underarm areas of the human body.

These and other features of the invention will become apparent from a consideration of the detailed description.

DETAILED DESCRIPTION OF THE INVENTION

As noted above, the invention is directed to oil-in-water (O/W) and water-in-oil (W/O) emulsions and microemulsions containing silanes or siloxanes having quaternary ammonium groups in their molecule as the oil phase. The silanes or siloxanes having quaternary ammonium groups are obtained by reacting (i) an organic quaternary ammonium compound having epoxide groups or halohydrin groups in its molecule, with (ii) a silane or siloxane having amino groups in its molecule. The reaction of components (i) and (ii) is carried out in the presence of (iii) a surfactant, with components (i)–(iii) being dispersed in (iv) an aqueous polar phase.

The Silanes & Siloxanes Containing Quaternary Ammonium Groups

These materials are essentially the reaction product obtained by combining components (i) and (ii). A detailed showing of their composition in terms of its structure can be found in detail in the '753 and '760 applications.

Generally, these materials can be described, for purposes herein, as being silanes or siloxanes having in their molecule at least one unit containing a group such as —R—Z—Q bonded to silicon in which:

R is a divalent hydrocarbon group such as ethylene,
Z is a group such as —N(Q1)—; and
Q is a group such as —CH(R)CH(OH)YN$^+$(R1)(R2)(R3) X$^-$;
wherein:
  Q1 is a monovalent hydrocarbon group such as methyl;
  Y is a divalent hydrocarbon group such as ethylene;
  X is a counter ion such as chloride Cl$^-$;
  and R1–R3 are monovalent hydrocarbon groups such as methyl.

A representative example therefore of at least one particularly preferred —R—Z—Q group is CH$_2$CH(OH)CH$_2$N$^+$(CH$_3$)$_2$(CH$_3$)Cl$^-$.

The Organic Quaternary Ammonium Compound with Epoxide Groups

Reference may be had to the '753 and '760 applications for a detailed showing of the generic formulas of compounds of this type. Suffice to say, for the purposes herein, some specific examples of useful compounds of this type are glycidyl trimethylammonium chloride and glycidyl trimethylammonium bromide. While non-terminal epoxides may also be used, terminal epoxides such as the compounds described are generally preferred. Combinations of epoxides may also be employed, as well as combinations of epoxides and the halohydrins noted below.

The Organic Quaternary Ammonium Compound with Halohydrin Groups

Again, reference may be had to the '753 and '760 applications for a detailed showing of the generic formulas of compounds of this type. Suffice to say, for the purposes herein, some specific examples of useful compounds of this type are (3-chloro-2-hydroxypropyl)trimethylammonium chloride $ClCH_2CH(OH)CH_2N(CH_3)_3Cl$, (3-chloro-2-hydroxypropyl)dimethyldodecylammonium chloride, (3-chloro-2-hydroxypropyl) dimethyloctadecylammonium chloride, (3-chloro-2-hydroxypropyl)trimethylammonium bromide, (3-chloro-2-hydroxypropyl)dimethyldodecylammonium bromide, and (3-chloro-2-hydroxypropyl) dimethyloctadecylammonium bromide.

While non-terminal halohydrins may also be used, terminal halohydrins such as the compounds described are generally preferred. Combinations of halohydrins may also be employed, as well as combinations of halonydrins and the epoxides noted above.

The Silanes & Siloxane with Amino Groups

Silanes containing amino groups for use herein generally comprise organosilicon monomers of the type $R_3SiR$ wherein the R groups in the molecule can consist of alkyl groups containing 1–6 carbon atoms, such as methyl, ethyl, propyl, isopropyl, butyl, and isobutyl; an aryl group such as phenyl; or the R groups can comprise amino groups such as aminoethyl, aminopropyl, aminoisobutyl, aminoethylaminopropyl, and aminoethylaminoisobutyl; provided at least one R group in the silane is an amino group.

Some representative examples of silanes containing amino groups which are suitable for use herein include aminomethyltrimethylsilane, aminotrimethylsilane, (benzylmethylamino)triethylsilane, diethylaminomethyltrimethylsilane, diethylaminotrimethylsilane, diethylaminotriphenylsilane, diisopropylaminotrimethylsilane, dimethylaminotriethylsilane, dimethylaminotrimethylsilane, phenylmethylbis (dimethylamino)silane, tetrakis(dimethylamino)silane, tri-n-hexylsilylamine, trimethylaminosilane, triphenylaminosilane, tris(dimethylamino)ethylsilane, tris (dimcthylamino)methylsilane, and tris(dimethylamino) phenylsilane.

Some examples of siloxanes with amino groups include those siloxane polymers and copolymers having number average molecular weights of 1,000–100,000, especially those having number average molecular weight of 5,000–50,000, such as aminopropyl terminated polydimethylsiloxanes and trimethylsilyl terminated dimethylsiloxane copolymers. The siloxanes should also contain 0.1–2.0 milliequivalents of amino functionality per gram of the siloxane on average, based on amino nitrogen of primary and secondary amino groups present in the siloxane. The amino groups may be present in the siloxane as aminoethyl groups, aminopropyl groups, aminoisobutyl groups, aminoethylaminopropyl groups, or aminoethylaminoisobutyl groups. Reference may be had to recently issued U.S. Pat. No. 6,475,974 (Nov. 5, 2002), for details of these and similar siloxanes containing amino groups, which can be used herein.

The Surfactant

Component (iii) used in the process is a surfactant, and this component may comprise a nonionic surfactant, a cationic surfactant, an anionic surfactant, or a mixture of such surfactants. Most preferred-however are nonionic surfactants.

Generally, the nonionic surfactant should be a non-silicon atom containing nonionic emulsifier. Most preferred are alcohol ethoxylates $R4-(OCH_2CH_2)_aOH$, particularly fatty alcohol ethoxylates. Fatty alcohol ethoxylates typically contain the characteristic group $—(OCH_2CH_2)_aOH$ which is attached to fatty hydrocarbon residue R4 which contains about eight to about twenty carbon atoms, such as lauryl ($C_{12}$), cetyl ($C_{16}$) and stearyl ($C_{18}$). While the value of "a" may range from 1 to about 100, its value is typically in the range of about 12 to about 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under trademarks and tradenames such as ALFONIC®, BRIJ, GENAPOL®, NEODOL®, SURFONIC®, TERGITOL®, and TRYCOL. Ethoxylated alkylphenols can also be used, such as ethoxylated octylphenol, sold under the trademark TRITON®.

Cationic surfactants useful in the invention include compounds containing quaternary ammonium hydrophilic moieties in the molecule which are positively charged, such as quaternary ammonium salts represented by $R'R''R'''R''''N^+ X^-$ where R', R", R'", and R"" are alkyl groups containing 1–30 carbon atoms, or alkyl groups derived from tallow, coconut oil, or soy; and X is halogen, i.e., chlorine or bromine. Most preferred are dialkyldimethyl ammonium salts represented by $R'R''N^+(CH_3)_2X^-$, where R' and R" are alkyl groups containing 12–30 carbon atoms, or alkyl groups derived from tallow, coconut oil, or soy; and X is halogen. Monoalkyltrimethyl ammonium salts can also be employed, and are represented by $R'N^+(CH_3)_3X^-$ where R' is an alkyl group containing 12–30 carbon atoms, or an alkyl group derived from tallow, coconut oil, or soy; and X is halogen.

Some representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under tradenames such as ADOGEN, ARQUAD, TOMAH, and VARIQUAT.

Among the various types of anionic surfactants which can be used are sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate (SDS); ether sulfates having alkyl groups of eight or more carbon atoms; and alkylaryl sulfonates having one or more alkyl groups of eight or more carbon atoms.

Some examples of commercial anionic surfactants useful in this invention include triethanolamine linear alkyl sulfonate sold under the tradename BIO-SOFT N-300 by the Stepan Company, Northfield, Ill.; sulfates sold under the tradename POLYSTEP by the Stepan Company; and sodium n-hexadecyl diphenyloxide disulfonate sold under the tradename DOWFAX8390 by The Dow Chemical Company, Midland, Mich.

The Aqueous Polar Phase

Component (iv) used in the process is one of (1) an aqueous phase consisting of water, (2) an aqueous phase containing water and a low molecular weight polysiloxane, preferably a volatile low molecular weight polysiloxane, and (3) an aqueous phase containing water and a polar solvent.

Some examples of suitable low molecular weight polysiloxanes include (a) low molecular weight linear and cyclic volatile methyl siloxanes, (b) low molecular weight linear and cyclic volatile and non-volatile alkyl and aryl siloxanes, and (c) low molecular weight functional linear and cyclic siloxanes. Most preferred, however, are low molecular weight linear and cyclic volatile methyl siloxanes (VMS).

VMS compounds have a structure corresponding to the average unit formula $(CH_3)_bSiO_{(4-b)/2}$ in which b has an average value of two to three. The compounds contain siloxane units joined by =Si—O—Si= bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have a structure corresponding generally to the formula $(CH_3)_3SiO\{(CH_3)_2SiO\}_cSi(CH_3)_3$. The value of c is 0–5. Cyclic VMS have the formula $\{(CH_3)_2SiO\}_d$. The value of d is 3–9. Preferably, these volatile methyl siloxane have a boiling point less than about 250° C. and viscosity of about 0.65 to about 5.0 mm²/s.

Representative linear volatile methyl siloxanes are hexamethyldisiloxane (MM) with a boiling point of 100° C., viscosity of 0.65 mm²/s, and formula $Me_3SiOSiMe_3$; octamethyltrisiloxane (MDM) with a boiling point of 152 ° C., viscosity of 1.04 mm²/s, and formula $Me_3SiOMe_2SiOSiMe_3$; decamethyltetrasiloxane (MD$_2$M) with a boiling point of 194° C., viscosity of 1.53 mm²/s, and formula $Me_3SiO(Me_2SiO)_2SiMe_3$; dodecamethylpentasiloxane (MD$_3$M) with a boiling point of 229° C., viscosity of 2.06 mm²/s, and formula $Me_3SiO(Me_2SiO)_3SiMe_3$; tetradecamethylhexasiloxane (MD$_4$M) with a boiling point of 245° C., viscosity of 2.63 mm²/s, and formula $Me_3SiO(Me_2SiO)_4SiMe_3$; and hexadecamethylheptasiloxane (MD$_5$M) with a boiling point of 270° C., viscosity of 3.24 mm²/s, and formula $Me_3SiO(Me_2SiO)_5SiMe_3$.

Representative cyclic volatile methyl siloxanes are hexamethylcyclotrisiloxane (D$_3$) a solid with a boiling point of 134° C. and formula $\{(Me_2)SiO\}_3$; octamethylcyclotetrasiloxane (D$_4$) with a boiling point of 176° C., viscosity of 2.3 mm²/s, and formula $\{(Me_2)SiO\}_4$; decamethylcyclopentasiloxane (D$_5$) with a boiling point of 210° C., viscosity of 3.87 mm²/s, and formula $\{(Me_2)SiO\}_5$; and dodecamethylcyclohexasiloxane (D$_6$) with a boiling point of 245° C., viscosity of 6.62 mm²/s, and formula $\{(Me_2)SiO\}_6$.

Representative branched volatile methyl siloxanes are heptamethyl-3-{(trimethylsilyl)oxy}trisiloxane (M$_3$T) with a boiling point of 192° C., viscosity of 1.57 mm²/s, and formula $C_{10}H_{30}O_3Si_4$; hexamethyl-3,3, bis {(trimethylsilyl)oxy} trisiloxane (M$_4$Q) with a boiling point of 222° C., viscosity of 2.86 mm²/s, and formula $C_{12}H_{36}O_4Si_5$; and pentamethyl {(trimethylsilyl)oxy} cyclotrisiloxane (MD$_3$) with the formula $C_8H_{24}O_4Si_4$.

Component (iv) may also include low molecular weight linear and cyclic volatile and non-volatile alkyl and aryl siloxanes represented respectively by the formulas $R_3SiO(R_2SiO)_nSiR_3$ and $(R_2SiO)_x$. R can be alkyl groups with 2–20 carbon atoms or aryl groups such as phenyl. The value of n is 0–80, preferably 5–20. The value of x is 3–9, preferably 4–6. These polysiloxanes have a viscosity generally in the range of about 1–100 mm²/s.

Polysiloxanes can also be used where n has a value sufficient to provide siloxane polymers with a viscosity in the range of about 100–1,000 mm²/sec. Typically, n can be about 80–375. Illustrative of such polysiloxanes are polydimethylsiloxane, polydiethylsiloxane, polymethylethylsiloxane, polymethylphenylsiloxane, and polydiphenylsiloxane.

Low molecular weight polysiloxanes containg functional groups can also be employed, and can be represented by structures corresponding to the formula $R_3SiO(RQSiO)_nSiR_3$ where Q is the functional group and n is generally the same as defined above. Examples of such functional polysiloxanes containing functional groups represented by Q are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

The polar solvents especially preferred herein are those compounds determined to be cosmetically acceptable non-aqueous polar solvents, among which are monohydroxy alcohols such as ethyl alcohol and isopropyl alcohol; diols and triols such as propylene glycol, 1,2-hexanediol $CH_3(CH_2)_3CH(OH)CH_2OH$, 2-methyl-1,3-propane diol $HOCH_2CH(CH_3)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols among which are PPG-14 butyl ether $C_4H_9[OCH(CH_3)CH_2]_{14}OH$. In applications other than personal care, these and other non-aqueous polar solvents can be employed.

The aqueous polar phase of the emulsion or microemulsion therefore, can consist of water, a mixture of water and a low molecular weight polysiloxane, or a mixture of water and a polar solvent which is preferably a polar organic compound. Generally, this component will be present in the composition in an amount to provide the balance of the composition to 100 percent, after taking in account the amounts of the other components used in formulating a suitable composition. Typically, however, this component will comprise 0.1–99.8 percent by weight based on the total weight of the O/W or W/O emulsion or microemulsion composition, preferably 1–80 percent by weight, and more preferably 3–10 percent by weight. While mixtures of liquids can be used to form this single phase component of the composition, liquids should be miscible and capable of forming an essentially homogeneous mixture.

Optional Components

Since emulsions and microemulsions are susceptible to microbiological contamination, a preservative may be required as an optional component of the composition, and some representative compounds which can be used include formaldehyde, salicylic acid, phenoxyethanol, DMDM hydantoin (1,3-dimethylol-5,5-dimethyl hydantoin), 5-bromo-5-nitro-1,3-dioxane, methyl paraben, propyl paraben, sorbic acid, imidazolidinyl urea sold under the name GERMALL® II by Sutton Laboratories, Chatham, N.J., sodium benzoate, 5-chloro-2-methyl-4-isothiazolin-3-one sold under the name KATHON CG by Rohm & Haas Company, Philadelphia, Penn., and iodopropynl butyl carbamate sold under the name GLYCACIL® L by Lonza Incorporated, Fair Lawn, N.J.

A freeze/thaw stabilizer can be included as another optional component of the composition including compounds such as ethylene glycol, propylene glycol, glycerol, trimethylene glycol, and polyoxyethylene ether alcohols such as RENEX 30 sold by ICI Surfactants, Wilmington, Del.

Another optional component of the composition which can be included is a corrosion inhibitor such as an alkanolamine, an inorganic phosphate such as zinc dithiophosphate, an inorganic phosphonate, an inorganic nitrite such as sodium nitrite, a silicate, a siliconate, an alkyl phosphate amine, a succinic anhyoride such as dodecenyl succinic anhydride, an amine succinate, or an alkaline earth sulfonate such as sodium sulfonate or calcium sulfonate.

Alternate Components

When O/W or W/O emulsion or microemulsion compositions according to this invention are used in particular product(s) intended for the personal care market, the compositions may be formulated to include one or more alternate components, for example:

(A) conditioning agents such as cationic polymers, proteins, natural oils, polysiloxanes other than quaternary ammonium functional polysiloxanes, hydrocarbon other than waxes, and mixtures thereof;

(B) cosurfactants such as betaines, monoalkylalkanolamides, dialkylalkanolamides, amine oxides, amine glycinates, amine propionates, amine sultaines, and mixtures thereof;

(C) polyhydric alcohols such as glycerin and sorbitol.

Products containing alternate components (A) are especially useful as conditioners, products containing (A) and (B) are especially useful as shampoos, and products containing (C) are especially useful as moisturizers.

Preparation

The amount of each of the various components used in preparing emulsions and microemulsions according to the invention, based on the total weight of the composition, is:

(i) 0.01–90 percent by weight of the organic quaternary ammonium compound having epoxide groups or halohydrin groups in its molecule;

(ii) 0.01–90 percent by weight of the silane or the siloxane having amino groups in its molecule;

(iii) 0.01–90 percent by weight of the surfactant, preferably 2–40 percent by weight, more preferably 5–20 percent by weight; and (iv) the balance to 100 percent by weight being the aqueous polar phase.

If an optional component is included, it is generally present in an amount of 0.01–0.1 percent by weight of each optional component, i.e., preservative, freeze/thaw stabilizer, or corrosion inhibitor.

The reaction can be made to take place by simply mixing all of the components together, and this is the minimum requirement to obtain reaction, i.e., to perform the "reacting" step under the circumstances. However, it is generally preferred to mix all of the reactants together and to heat them. A catalyst is typically not necessary but under some circumstance, an appropriate catalyst may be employed. In this regard, it has been found that in general, tertiary amines do not add readily to epoxides. This can be improved if the reaction mixture is acidified, especially in stoichiometric proportions, or the tertiary amine is pretreated with an acid in order to convert it to its acid salt.

The emulsions and microemulsions can be prepared using simple propeller mixers, turbine-type mixers, Brookfield counter-rotating mixers, or homogenizing mixers. No special equipment or processing conditions are generally required.

EXAMPLES

The following examples are set forth in order to illustrate the invention in more detail.

Example 1

Synthesis in a Microemulsion

A quaternary ammonium functional siloxane was prepared from a 3000 cS (mm$^2$/s) dimethylsiloxane copolymer containing about two mole percent aminoethyl/aminoisobutyl/methylsiloxane units. It contained repeat units with both primary and secondary amine groups. Each aminoethyl/aminoisobutyl/methylsiloxane unit is theoretically capable of reacting with from 1–3 equivalents of glycidyl trimethylammonium chloride. Although the preferred site of the reaction was not determined, a 167 percent stoichiometry would be sufficient to react one quarter of the NH groups on all of the primary amine sites.

Accordingly, 20.13 gram of the amino functional siloxane described above (0.7219 meq amine/g), 0.73 gram of glycidyl trimethylammonium chloride solution containing about 75 percent by weight of the active in water, 4.00 gram of TERGITOL® TMN 10 nonionic surfactant, 2.02 gram of TERGITOL® TMN 6 nonionic surfactant, and 4.00 gram of water, were weighed and placed into ajar. The reaction mixture was heated in a 70° C. water bath, stirred with a magnetic stir bar, and these conditions were maintained for 3.5 hours. On cooling, a $^{13}$C Nuclear Magnetic Resonance Spectroscopy ($^{13}$C NMR) was carried out. It showed a spectrum consistent with spectrums obtained in the '760 application. The composition was a water-in-oil (W/O) microemulsion, which when diluted with water, yielded a stable oil-in-water (O/W) emulsion.

Example 1A

Synthesis in an Emulsion 100.18 gram of the amino functional siloxane used in Example 1(0.7219 meq amine/g), 7.38 gram of glycidyl trimethylammonium chloride solution containing 75 percent by weight of active in water, 2.03 gram of TERGITOL® TMN 10, 2.01 gram of TERGITOL® TMN 6, and 2.00 gram of water, were weighed and placed into a three neck 500 ml flask. The reaction mixture was heated to 70° C. while stirring under static nitrogen. It was maintained under these conditions for 3.5 hours. 226.8 gram of water were added to the resulting composition, and when it was mixed, it produced a stable O/W emulsion.

Example 2

Synthesis in an Emulsion 20.5 gram of an amino functional siloxane of the type used in Example 1 (with 0.7219 meq amine/g), 1.5 gram of glycidyl trimethylammonium chloride solution containing 75 percent by weight of the active in water, 3.0 gram of TERGITOL® TMN 10, 3.1 gram of TERGITOL® TMN 6, and 4.3 gram of water, were weighed and placed into a beaker. The reaction mixture was mixed with a mechanical mixer at 1200 rpm for 3 minutes. An additional portion of 35.9 gram of water was added. The mixing was continued but at a speed 5 of 500 rpm for 5 minutes. It was placed in a vial and heated at 70° C. for 3 hours. The resulting composition was a stable O/W emulsion.

Example 3

Synthesis in an Emulsion—Product With Higher Content of Quaternary Ammonium Functionality 90.2 grams an amino functional siloxane of the type used in Example 1 (0.729 meq amine/g), 10.9 gram of glycidyl trimethyl ammonium chloride solution containing 75 percent by weight of active in water, 2.4 gram of TRITON® X-405, 27.4 gram of TERGITOL® TMN 6, and 20.4 gram of water, were weighed and placed into ajar. The jar was shaken by hand to mix the ingredients instead of mixing them mechanically. The result was a clear and uniform mixture. The mixture was placed in an 80° C. oven for two hours, and a stable W/O emulsion was produced.

Example 4

Synthesis in an Emulsion using a Single Surfactant

A quaternary ammonium functional siloxane was prepared from a 150 cS ($mm^2/s$) dimethylsiloxane copolymer containing about two mole percent aminoethyl/aminoisobutyl/methylsiloxane units. It contained repeat units with both primary and secondary amine groups. Each aminoethyl/aminoisobutyl/methylsiloxane unit is theoretically capable of reacting with from 1–3 equivalents of glycidyl trimethylammonium chloride. Although the preferred site of the reaction was not determined, a 33 percent stoichiometry would be sufficient to react one quarter of the NH groups on all of the primary amine sites.

Accordingly, 308.02 grams of this amino functional siloxane (0.5034 meq amine/g), 18.0 gram of glycidyl trimethyl ammonium chloride solution containing 75 percent by weight of active in water, 42.11 gram of TERGITOL® TMN 6, and 35.97 gram of water, were weighed and placed into ajar. The jar was shaken by hand to mix the ingredients instead of mixing them mechanically. The result was a clear and uniform mixture. The mixture was placed in an 80° C. oven for two hours, and a stable W/O emulsion was produced.

Example 5

Synthesis in an Emulsion—Product With Diol Functionality 91.0 gram of an amino functional siloxane of the type used in Example 1 (0.729 meq amine/g), 5.7 gram of glycidyl trimethyl ammonium chloride solution containing 75 percent by weight of active in water, 3.5 gram of glycidol (2,3-epoxy-1-propanol), 12.9 gram of TRITON® X-405, 17.3 gram of TERGITOL® TMN 6, and 24.6 gram of water, were weighed and placed into ajar. The jar was shaken by hand to mix the ingredients instead of mixing them mechanically. The result was a clear and uniform mixture. The mixture was placed in an 80° C. oven for two hours, and a stable W/O emulsion was produced.

Example 6

Hair Conditioner Formulations

Samples of quaternary ammonium functional siloxanes were added to rinse-off conditioning formulations using about two percent by weight of the quaternary ammonium functional siloxane. The conditioning formulations are shown in Table 1. In the table, Conditioner A contained no silane or siloxane. Conditioner B contained a quaternary ammonium functional siloxane according to the present invention. Conditioner C contained an amine-functional siloxane emulsion for comparison.

TABLE 1

| Ingredient | Conditioner A Weight Percent | Conditioner B Weight Percent | Conditioner C Weight Percent |
|---|---|---|---|
| Deionized Water | q.s. to 100% | q.s. to 100% | q.s. to 100% |
| Hydroxyethylcellulose | 1.5 | 1.5 | 1.5 |
| Cetearyl Alcohol | 1.0 | 1.0 | 1.0 |
| PEG-100 Stearate & Glyceryl Stearate | 1.0 | 1.0 | 1.0 |
| Siloxane of Example 5 | — | 2.0 | — |
| Amino Siloxane Emulsion | — | — | 2.0 |
| DMDM Hydantoin | 0.2 | 0.2 | 0.2 |

In Table 1, hydroxyethylcellulose functioned as a thickener, and was present in the formulation as the commercially available material sold under the trademark NATROSOL® 250 MR by Hercules Incorporated, Wilmington, Del. Cetearyl alcohol functioned as a emulsion stabilizer and was present as a commercially available material sold under the tradename LANETTE O by Cognis Corporation, Hoboken, N.J. The nonionic surfactant PEG-100 Stearate & Glyceryl Stearate was present as a commercially available material sold under the trademark ARLACEL® 165 by Uniqema Americas, Wilmington, Del. The amount of the siloxane of this invention obtained in Example 5 was present in Conditioner B in a concentration based on level of siloxane active in the conditioner. The amino siloxane emulsion was used for comparison and comprised a commercially available cationic emulsion containing about 35 percent of an amine-functional silicone polymer which is used for providing conditioning benefits to the hair. The preservative dimethylol-dimethyl (DMDM) hydantoin was a commercially available material sold under the trademark GLYDANTO® by Lonza Incorporated, Fairlawn, N.J.

Procedure

Preparation of Hair Sample

Slightly bleached European human hair from International Hair Importer and Products, Inc., was used for testing the conditioners prepared herein. A master hand of hair about eight inches in length was subdivided into a series of individual hair tresses. Each tress weighed about 2.5 grams. A 0.5 inch (1.27 cm) of the root end of the hair was trimmed and glued to a 2 inch by 2 inch (5.08 cm by 5.08 cm) plastic tab using DUCO CEMENT ®. The cement was allowed to dry, and the hair tress was combed and trimmed to a length such that six inches (15.24 cm) of hair extended below the bottom of the plastic tab. A hole was punched in middle of tab about one fourth inch (0.635 cm) from its top. Each tress was rinsed for 15 seconds under 40° C. tap water. Using a pipette, 1.0 gram of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures.

INSTRON procedures are standard, recognized, and industrially acceptable protocols, see for example, U.S. Pat. No. 5,389,364 (Feb. 14, 1995), U.S. Pat. No. 5,409,695 (Apr. 25, 1995), U.S. Pat. No. 5,419,627 (May 30, 1995), and U.S. Pat. No. 5,504,149 (Apr. 2, 1996).

For tests involving rinse-off conditioners, hair tresses are rinsed with tap water for 30 seconds at 40° C. The test conditioner is applied to the tress in the amount of 0.8 gram, and the tress is stroked for 30 seconds. The tress is rinsed for 30 seconds under tap water at 40° C.

Excess water is removed by pulling the tress through the index and middle fingers of the hand. The tresses are allowed to dry separately on a paper towel overnight at room temperature. The tresses are combed once before performing an INSTRON study.

Test Procedure

INSTRON COMBING is an industry recognized test for determining hair conditioning by the ease of wet combing and the case of dry combing. The test employs an INSTRON strain gauge, which is equipped to measure the force required to comb the hair. The conditioning performance is based on the ability of a particular hair treatment formulation, such as a shampoo or a hair conditioner, to reduce the force required to comb the hair with the INSTRON strain gauge. The force is reported as an Average Combing Load (ACL). The lower the number of the ACL value, the better is the conditioning effect imparted by the formulation being tested. Typically, ACL baselines are initially established using untreated tresses that have only been washed with a sodium lauryl sulfate solution. The effectiveness of a treatment can then be expressed as an ACL of the treated tress or percent reduction in ACL, calculated using the relationship:

(untreated hair ACL−treated hair ACL)×100 divided by the untreated hair ACL

According to the INSTRON WET COMBING method, hair is first wetted by dipping it into distilled water, and then the hair is detangled by combing the tress three times. The tress is then retangled by dipping in distilled water three times. Excess water is removed by passing the tress through the index and middle fingers of the hand twice. The tress is placed on a hanger and INSTRON combed. Retangling and INSTRON combing are repeated until all data points are collected. An average combing force of three tresses is measured for each treatment.

The results of INSTRON WET COMBING using Conditioners A–C according to the present application are shown in Table 2. It can be seen that the quaternary ammonium functional siloxane, i.e., Conditioner B, provided a large reduction in wet combing forces compared to control Conditioner A without a silane or siloxane, and Conditioner C which contained an amino functional silicone emulsion. Conditioner B therefore is capable of improving the conditioning properties of hair.

According to the INSTRON DRY COMBING method, hair is detangled by combing the tress 3 times. Then hair is retangled by swirling the tress clockwise 3 times and swirling it counter clockwise 3 times. The tress is then placed on a hanger and INSTRON combed. Retangle and Instron combing are repeated until all data points are collected. An average combing force for three tresses is measured for each treatment.

The results of INSTRON DRY COMBING tests conducted with Conditioners A–C are shown in Table 3. Table 3 shows that the quaternary ammonium functional siloxane of the present invention provided a large reduction in dry combing forces, compared to control Conditioner A and comparison Conditioner C. Conditioner B is therefore capable of improving the conditioning properties of hair.

TABLE 2

INSTRON WET COMBING

| Conditioner | ACL Reduction, Percent |
| --- | --- |
| A | −67 |
| B | 89 |
| C | 79 |

TABLE 3

INSTRON DRY COMBING

| Conditioner | ACL Reduction, Percent |
| --- | --- |
| A | −10 |
| B | 63 |
| C | 58 |

The emulsions and microemulsions prepared herein are useful in personal care, for example, in preparing compositions such as antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair sprays, mousses, permanents, depilatories, and cuticle coats. In cosmetics, the compositions can be added to make-ups, color cosmetics, foundations, blushes, lipsticks, eyeliners, mascara, oil removers, color cosmetic removers, and powders. In such applications, the compositions may include oil soluble, polar solvent soluble, and water soluble ingredients such as vitamins.

The emulsions and microemulsions are also capable of functioning as carriers for pharmaceuticals, biocides, herbicides, pesticides, and other biologically active substances; and such compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making oil-in-water (O/W) and water-in-oil (W/O) emulsions and microemulsions containing silanes or siloxanes having quaternary ammonium groups in their molecule as the oil phase of the emulsion or microemulsion, comprising reacting (i) an organic quaternary ammonium compound having epoxide groups or halohydrin groups in its molecule, with (ii) a silane or siloxane having amino groups in its molecule, in the presence of (iii) a surfactant, components (i)–(ii) being dispersed in (iv) an aqueous polar phase.

2. A method according to claim 1 in which the organic quaternary ammonium compound having epoxide groups is glycidyl trimethylammonium chloride or glycidyl trimethylammonium bromide.

3. A method according to claim 1 in which the organic quaternary ammonium compound having halohydrin groups is selected from the group consisting of (3-chloro-2-hydroxypropyl)trimethylammonium chloride, (3-chloro-2-hydroxypropyl)dimethyldodecylammonium chloride, (3-chloro-2-hydroxypropyl) dimethyloctadecylammonium chloride, (3-chloro-2-hydroxypropyl)trimethylammonium bromide, (3-chloro-2-hydroxypropyl)dimethyldodecylammonium bromide, and (3-chloro-2-hydroxypropyl) dimethyloctadecylammonium bromide.

4. A method according to claim 1 in which the aqueous polar phase consists of water.

5. A method according to claim 1 in which the aqueous polar phase comprises water and a volatile low molecular weight polysiloxane.

6. A method according to claim 1 in which the aqueous polar phase comprises water and a polar organic compound.

7. A method according to claim 6 in which the polar organic compound is selected from the group consisting of monohydroxy alcohols, diols, triols, glycerol esters, and polyglycols.

8. A method of treating hair, skin, or underarm comprising applying to hair, skin, or underarm, an emulsion or microemulsion prepared according to claim 1.

* * * * *